United States Patent [19]

Hindla

[11] Plant 4,535

[45] May 13, 1980

[54] AZALEA PLANT

[76] Inventor: Louis A. Hindla, 986 Church St., Bohemia, N.Y. 11716

[21] Appl. No.: 13,541

[22] Filed: Feb. 21, 1979

[51] Int. Cl.[2] ..... A01H 5/00

[52] U.S. Cl. ..... Plt./56

[58] Field of Search ..... Plt./56, 55

*Primary Examiner*—Robert E. Bagwill

*Attorney, Agent, or Firm*—Frank B. Robb

[57] ABSTRACT

There is disclosed an azalea plant having flower and growth habit similarity to a known variety *Azalea kaempferi* "Fedora" an unpatented variety, and foliage characteristics of a Kurume Azalea Hinodegiri, also an unpatented variety, distinguished however by the abundant flowers of purplish pink color with a pronounced white stripe on the reverse of each petal extending from the base at the center thereof to the extremity, the glossy, dark green foliage which is retained well in winter, and the upright habit of growth which makes it stand out among other low growing varieties.

2 Drawing Figures

DESCRIPTION OF THE INVENTION

My present invention relates to a new and distinct variety of azalea plant which originated as a seedling which is believed to be the result of open pollination of *Azalea kaempferi* known as "Fedora" (an unpatented variety) and Azalea Kurume "Hinodegiri" (also unpatented) growing in a planting which was being cultivated by me, in Bayport, Long Island.

After selecting my new and distinct variety, which I designate "Pink Radiance", I have carefully cultivated the same and personally caused the same to be asexually reproduced in my nursery at Bohemia, N.Y., and have thereby established that the distinguishing characteristics to be set forth hereinafter are held through successive propagations.

My new variety of azalea plant is distinguished from the other varieties with which it was originally grown and of which the variety "Fedora" is denominated the seed parent, the "Hinodegiri" variety being the pollen parent, as evidenced by the unique combination of principal characteristics which are outstanding in my new variety and which make it a valuable addition to the various Azalea varieties known to me, among those characteristics being the following:

1. The glowing purplish pink color of the blooms wherein the reverse of each petal includes a distinct almost white stripe extending from the base in the center of the petal;

2. The abundance of blooms borne three or four in irregular, rounded clusters on strong stems;

3. The strong upright habit which makes the entire plant stand out when grown with low growing varieties;

4. The long lasting, superior foliage which is evergreen is retained well throughout the year whereas the parent "Fedora" is almost deciduous.

5. The adaptability of the variety to container culture.

The radiant quality of the bloom of my new variety cannot be emphasized too much and the white stripe on the reverse of the petals which begins to make a definite appearance during the late development of the buds, clearly adds to the attractiveness, giving a luminous appearance, the flowers being arranged with three to four florets per group, occasionally only two, the florets being about 2 9/16" across and 1⅜" high, with five rounded lobes per floret. The group of three florets may be about 3¼" across and 3" high.

In the accompanying drawing I have shown the flowers of a typical blooming plant of my new variety, a pair being individually illustrated as viewed from virtually beneath the same, in the upper view and in the lower view a typical plant of my new variety with the flowers in bloom thereon, and depicted in colors which are as nearly true as is possible to make the same in a color illustration of this character, bearing in mind that the colors designated hereinafter, are according to my personal comparison.

There follows a description of my new variety, with color terminology where applicable in accordance with comparisons made with the Nickerson Color Fan, published by Munsell Color Company, of Baltimore, Md., except where general color terms which have ordinary dictionary significance are applicable and appropriate.

My new variety of azalea plant has been asexually reproduced by cuttings in the vicinity of Bohemia, N.Y., and continually reproduced to the present time.

DESCRIPTION

Parentage: Seedling.

Seed parent: *Azalea kaempferi* "Fedora" (unpatented).

Pollen parent: Azalea "Hinodegiri" (unpatented).

Propagation: Holds its distinguishing characteristics through succeeding propagation by cuttings.

Locality where grown and observed: Bohemia, N.Y.

Plant:

*Form.*—Upright.

*Growth habit.*—Upright and bushy.

*Rooting habit.*—Usual fibrous root system.

*Blooming habit.*—Profuse.

*Blooming season.*—Mid-May.

Foliage:

*Size.*—Medium.

*Quantity.*—Abundant.

*Color.*—New foliage — upper side — light green. under side — light green, about the same as upper side. Old foliage — upper side — dark green and glossy. Under side — dark green, somewhat lighter than upper side.

*Shape.*—Broadly elliptic.

*Texture.*—Upper side — glossy. Under side — smooth.

*Edge or margin.*—Shape — $1\frac{1}{2}'' \times 1''$ — broadly elliptic, new leaves oblanceolate.

Disease resistance: During the observations over a period of years, the plant is very resistant to the usual diseases associated with azaleas.

Flower:

*Borne.*—Three or four to a stem in irregular rounded clusters; stems strong and medium length.

*Quantity of bloom.*—Abundant when grown outdoors.

*Continuity.*—One season.

*Permanence.*—10 to 14 days.

*Petalage.*—Number of petals under normal conditions — five. Color — between strong purplish pink 5 RP 6/10 and strong purplish pink 7.5 RP 7/10.

*Texture.*—Heavy substance.

*Appearance.*—Inside — between strong purplish pink 5 RP 6/10 and 7.5 RP 7/10; slightly deeper spotting. Outside — between strong purplish pink 5 RP 6/10 and strong purplish pink 7.5 RP 7/10 with almost white stripe on reverse side of each lobe.

*Shape.*—Funnel-shaped — about 2 9/16″ across × $1\frac{3}{8}''$ high.

*Arrangement.*—3 to 4 florets per group; occasionally two; $3\frac{1}{4}''$ across to 3″ high with 5 rounded lobes per floret.

Bud: Long-pointed about 1″ with the white stripe showing in late stages of development.

Reproductive organs:

*Stamens.*—5 curved; uneven. Color — between strong purplish pink 5 RP 6/10 and strong purplish pink 7.5 RP 7/10.

*Pollen.*—Color — yellow.

*Styles.*—Between strong purplish pink 5 RP 6/10 and strong purplish pink 7.5 RP 7/10.

*Ovaries.*—Green.

I claim:

1. A new and distinct variety of azalea plant, substantially as herein shown and described, characterized particularly as to novelty by the unique combination of purplish pink flowers borne in abundance in irregular rounded clusters on strong stems, the reverse of each flower petal having a nearly white stripe extending from the base at the center thereof, the evergreen, glossy dark green foliage retained well in winter, and the tall upright habit.

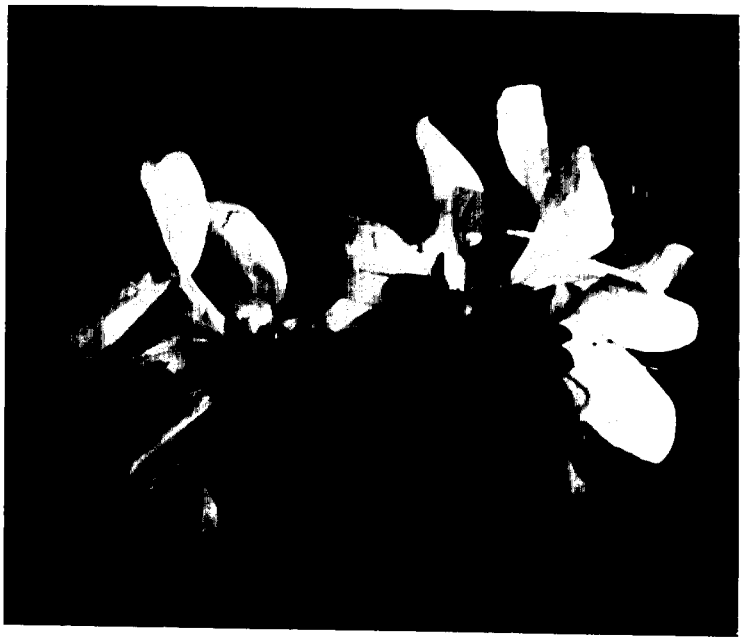
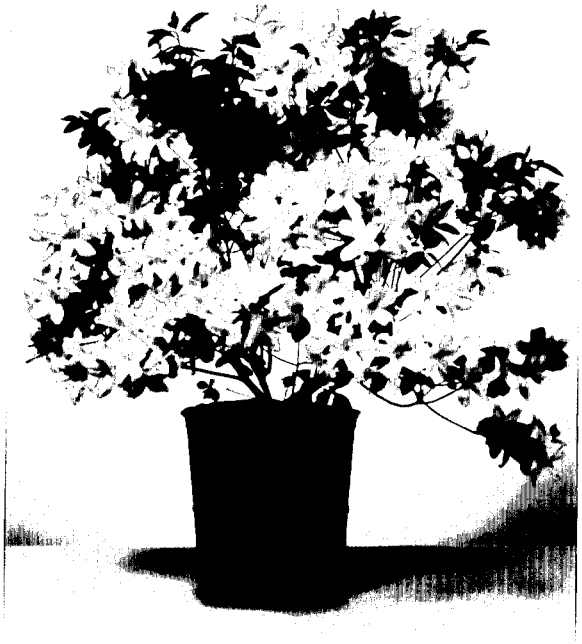

* * * * *